United States Patent [19]

Carlos et al.

[11] 4,207,771
[45] Jun. 17, 1980

[54] METHOD AND APPARATUS FOR MONITORING CRACKING USING STRESS WAVE EMISSION TECHNIQUES

[75] Inventors: Mark F. Carlos, Hamilton Township, Mercer County; Min-Chung Jon; Vito Palazzo, both of East Windsor Township, Mercer County, all of N.J.

[73] Assignee: Western Electric Company, Inc., New York, N.Y.

[21] Appl. No.: 16,686

[22] Filed: Mar. 2, 1979

[51] Int. Cl.² ............................................. G01N 29/04
[52] U.S. Cl. ....................................................... 73/587
[58] Field of Search ................. 73/587, 588, 590, 801; 340/566

[56] References Cited

U.S. PATENT DOCUMENTS

| | | | |
|---|---|---|---|
| 3,713,127 | 1/1973 | Kelroy et al. | 340/566 |
| 3,858,439 | 1/1975 | Nakamura | 73/587 |
| 3,903,512 | 9/1975 | Laymon | 340/566 |
| 3,924,456 | 12/1975 | Vahaviolos | 73/801 |
| 4,054,867 | 10/1977 | Owens | 73/587 |
| 4,086,816 | 5/1978 | Jon et al. | 73/587 |

Primary Examiner—Anthony V. Ciarlante
Attorney, Agent, or Firm—D. J. Kirk

[57] ABSTRACT

The disclosure is directed to a technique for monitoring signals emanating from a ceramic article (10) during a soldering operation. In order to determine whether the signals are stress wave emissions (SWE's) or noise the number of pulses (41) of the monitored signal having an amplitude exceeding a preset threshold (51), during a period of time, are counted. A count (62) proportional to the area under the envelope of the detected signal during the period of time is also made. A ratio of the count related to the area under the envelope to the pulse count is formed and compared to an empirically developed range of ratios which are indicative of a stress wave emission signal.

9 Claims, 6 Drawing Figures

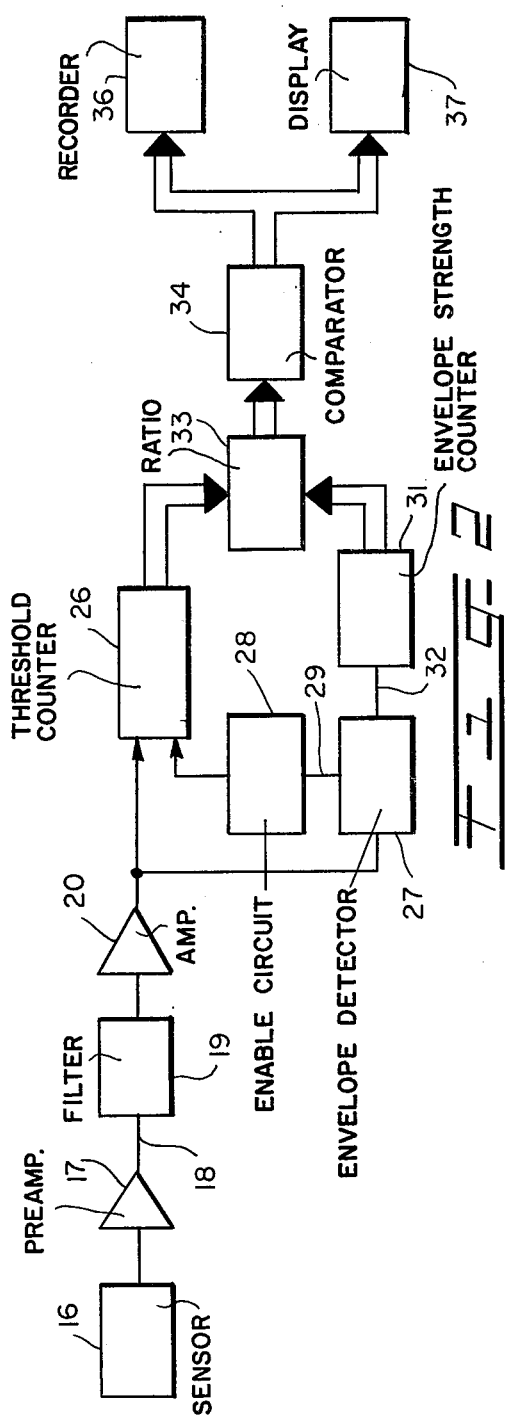
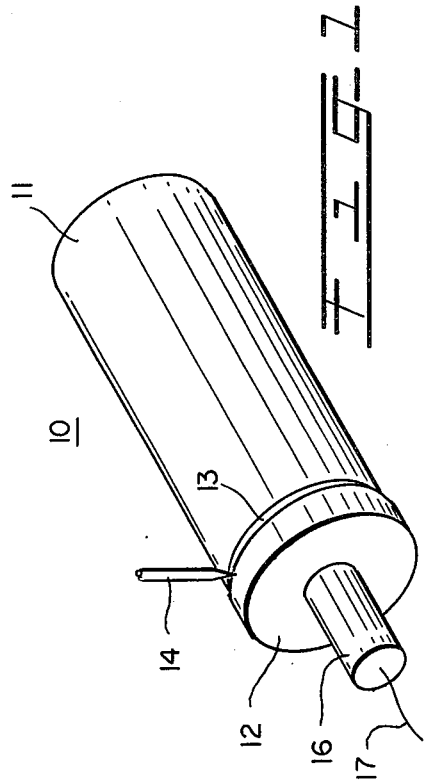

METHOD AND APPARATUS FOR MONITORING CRACKING USING STRESS WAVE EMISSION TECHNIQUES

TECHNICAL FIELD

This invention relates to a method for the real-time, non-destructive evaluation of bonds. In particular, the invention is directed to a system for monitoring cracks which may occur during the bond formation, using Stress Wave Emission (SWE) techniques.

BACKGROUND OF THE INVENTION

Ceramic materials have been used extensively in fabricating integrated circuits and the like. Because of their low resistance to externally exerted forces, ceramics of poor quality tend to crack due to thermal or mechanical shock during soldering or machining operations. Since it is of the utmost importance that ceramic components be of high quality, a technique for non-destructively detecting the cracking of parts which may not be visually accessible during processing is highly desirable.

U.S. Pat. No. 3,924,456, which issued on Dec. 9, 1975 to S. J. Vahaviolos and is assigned to the instant assignee, is directed to detecting microcracks in ceramic substrates using SWE techniques. An SWE, also referred to as an Acoustic Emission, may be defined as an elastic wave propagated in a structure as the result of an applied stress and which is characterized by low amplitude, short duration and fast rise time. A stress wave event, caused by a crack, has an initial high pulse which is followed by a series of lower amplitude pulses having an exponentially decaying envelope. An SWE signal may comprise a multitude of such events.

The Vahaviolos patent describes a piezoelectric transducer mounted proximate the substrate, which is subjected to a load, to detect stress waves emitted from the microcracks as they form. A processing circuit generates an output signal indicative of a detected crack when the magnitude of the electrical output from the transducer exceeds a predetermined system noise level.

Such a technique has been found to be most effective when the system noise levels are low. However, at times, the ambient noise vibration due to automatic soldering tools, bonders or associated mechanical movements can have the same amplitude or even a greater amplitude than the SWE events. These mechanical vibrations translate into relatively high oscillating signals which can be incorrectly interpreted by the stress wave detection apparatus as being caused by a crack in the material, resulting in loss of acceptable product.

U.S. Pat. No. 4,086,816 which issued on May 2, 1978 to Jon et al. and is also assigned to the instant assignee is directed to distinguishing between SWE signals and noise signals. That patent teaches the counting of detected signal pulses passing through a threshold during a predetermined period of time while simultaneously counting the number of excursions of the envelope of the pulses passing through the threshold. A ratio of the signal pulse count to the envelope excursion count made during the same time period is formed and compared to an empirically determined range of ratios which are indicative of an SWE signal.

The technique disclosed in the Jon et al. patent has been most successful. However, there are instances where certain noise signals may yield a ratio that falls within the range of ratios indicative of an SWE signal. Such noise signals may, for instance, have a pattern that differs from an SWE event but will have substantially the same pulse frequency which will result in the same pulse count and a pulse count-to-envelope excursion count indicative of an SWE signal.

Thus, there exists a need for a technique that can distinguish between SWE signals and noise signals in substantially all situations, including the situation where the noise has a different pattern than the SWE signal but has substantially the same pulse count.

SUMMARY OF THE INVENTION

The instant invention overcomes the foregoing problem with a method of determining, during an operation, whether a detected signal is an SWE signal. The method comprises the steps of (a) determining a first value that is proportional to the number of pulses of the detected signal above a preset threshold during a period of time; (b) determining a second value that is proportional to the area under the envelope of the detected signal during said time period; (c) forming a ratio of the area value to the pulse value; and (d) comparing the ratio so formed to a predetermined range of ratio values which are indicative of a stress wave emission.

Advantageously, the instant technique makes it possible to detect SWE signals caused by cracking in a noisy environment where the detected SWE signal can be smaller than the random mechanical noise of the bonding apparatus or other noise.

BRIEF DESCRIPTION OF THE DRAWING

FIG. 1 is a perspective view of a metallic cap being soldered to a ceramic housing;

FIG. 2 is a block diagram of SWE detection apparatus which embodies the instant invention.

DETAILED DESCRIPTION

Figure 3:
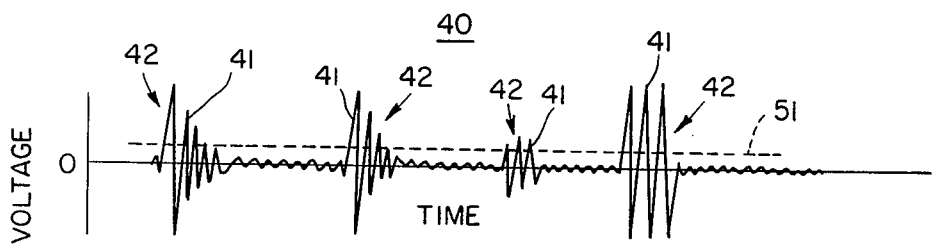
FIGS. 3 to 6 are representations of waveforms appearing during various stages of the instant method.

The instant invention will be described in relation to a real-time, non-destructive technique for monitoring a ceramic housing, during a soldering operation thereon, for SWE signals which are indicative of cracking. However, it will be understood that such description is exemplary only and is for the purpose of exposition and not for the purpose of limitation. It will be readily appreciated that the instant techniques are equally applicable to distinguishing mechanical noise from SWE signals in other operations involving bonding, testing or the like where a stress is induced in a material.

The exemplary embodiment of the instant invention shown in FIG. 1 depicts a high voltage capacitor 10 having a cylindrical ceramic housing 11 to which a metallic end cap 12 is to be permanently affixed. The housing 11 has a band of solder 13 predeposited about the periphery thereof and the end cap 12 is urged onto the housing into intimate contact with a portion of the solder. A soldering iron tip 14 is brought into contact with the cap 12 which is heated to cause the solder 13 to reflow. The tip 14 is then moved circumferentially about the housing 11 causing the solder 13 to reflow and bond the metallic cap 12 to the ceramic housing.

A one MHz piezoelectric sensor 16 using a lead zirconate-lead titanate K-350 crystal purchased from Keramos, Inc. operating in the thickness vibrational mode is placed in intimate contact with the end cap 12 and is connected to a low noise preamplifier 17 (see FIG. 2). The preamplifier 17 should be located as close as possible to the sensor 16 in order to keep noise and attenuation due to long cable lengths to a minimum. The preamplifier 17 supplies a constant gain of 40 db in the range of frequencies from 100 KHz to 2 MHz and is capable of driving a 50 ohm coaxial cable 18. The output of the preamplifier 17 is electrically connected to the serial combination of a filter 19 and an amplifier 20. The filter 19 is a third order high pass, passive type which filters out unwanted lower frequency noise (i.e., below 500 KHz) such as the hitting or scraping of the soldering iron tip 14 against the ceramic housing 11. The amplifier 20 is a low noise 715 type having a gain set at 40 db for signals in the range of 100 KHz to 2 MHz.

The amplifier 20 is connected in parallel to a threshold crossing counter 26 and an envelope detector 27. An enable circuit 28 connects a first output 29 of the envelope detector 27 to the threshold crossing counter 26. An envelope strength counter 31 has an input lead 32 from the envelope detector 27 and has an output connected to a ratio forming circuit 33 which also receives the output of the threshold crossing counter 26. The output of the ratio forming circuit 33 is connected to a comparator 34 which may be connected to a recording apparatus 36 and/or a display apparatus 37.

In operation, as heat is applied by the soldering iron tip 14 (FIG. 1) to reflow the solder 13, the sensor 16 detects SWE signals emanating from the heated portion of the ceramic housing 11. The SWE signals are transmitted through end cap 12 and are converted into electrical signals by the sensor 16. The electrical signals are processed by the amplifiers 17 and 20 as well as the filter 19 and may result in a signal similar to waveform 40 shown in FIG. 3. The signals represented by the waveform 40 enter the threshold crossing counter 26 and the excursions of the individual pulses 41 in an event 42 above a threshold 51 are counted (see FIG. 5) during a time period defined by an enable signal from the enable circuit 28.

The waveform 40 is simultaneously presented to the envelope detector 27 which forms a positive envelope 43 (FIG. 4) of the waveform 40. A "start" signal is sent to the enable circuit 28 over the lead 29 in response to a positive-going excursion of the envelope 43 (see FIG. 4) through threshold 51 and a "stop" signal is sent at the time of a negative-going excursion of the envelope through the threshold. An enable signal is presented to the threshold crossing counter 26 from the enable circuit 28 causing the counter to count the pulses only during the enable period (i.e., the time that the envelope 43 is above the threshold 51). A signal pulse count 63 is shown in FIG. 5.

Figure 6:
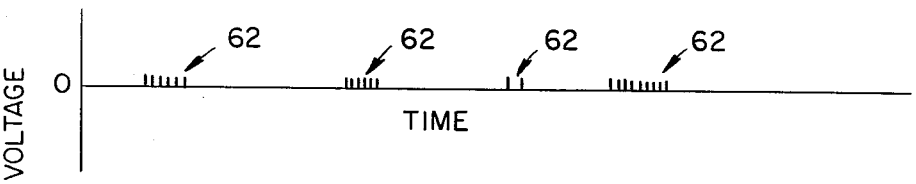

The envelope 43 is forwarded to the envelope strength counter 31 which converts the area (amplitude and length of time) under that portion of the envelope 43 that is above the threshold 51 into a proportional number of digitized pulses 62 (see FIG. 6). The strength counter 31 may be a model 4707, Teledyne Philbrick 5 Megahertz voltage-to-frequency converter, or the like, having a dynamic range from 100 Hertz to 5 Megahertz for corresponding inputs of 1 millivolt to 10 volts. The converter converts the analog input signal (i.e., envelope 43) into a series of digital pulses having a period which decreases in direct proportion to the increase in the amplitude of the input signal. The strength counter 31 provides a count for each event 42.

The count from the envelope strength counter 31 and the signal pulse count from the threshold counter 26 are forwarded to the ratio forming circuit 33 where the ratio of the strength count to the signal pulse count is accomplished. The ratio forming circuit 33 may be any well-known divider circuit or microprocessor arranged to perform a division operation. The ratio so determined is compared to a predetermined range of empirically developed values of ratios in the comparator 34 to determine whether the signal is an SWE signal or noise. The comparator 34 may be an SN7485 comparator manufactured by the Texas Instruments Corporation. In one embodiment, ratios falling within a range from approximately 1.6 to 2.5 were found to be indicative of SWE signals. This range may differ depending on particular applications and circuitry used and should be empirically developed for each application.

The ratios and the counts used to form the ratios may be forwarded to the recorder 36 to form a permanent record. Additionally, the ratios indicative of a detected SWE signal may be forwarded to the display circuit 37 and an audible and/or visual alarm activated. A readout is provided for each SWE or noise event 42 having an envelope 43 with an amplitude that exceeds the threshold 51.

Advantageously, the ratio of the signal envelope strength count 62 (i.e., area under the positive envelope 43) to the pulse count 63 has been found to provide a more accurate indication of the pattern of the detected signal. Each SWE event 42 is comprised of an initial high amplitude pulse with a number of subsequent pulses having decreasing amplitude. A multitude of such events may occur during operations such as thermocompression bonding, welding or the like. Prior art techniques are directed to counting the events and/or pulses which cross a predetermined threshold and relate that count to the quality of the weld. However, such counts may also include noise. The present technique takes into account the pattern of each event by measuring the strength (i.e., area under the envelope of the event).

Figure 4:
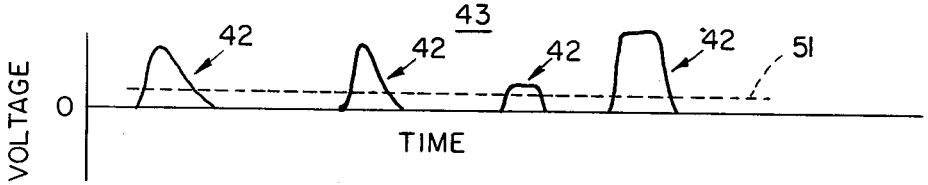
Figure 5:
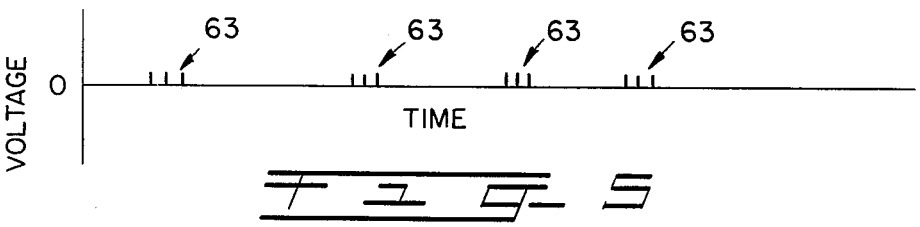

For instance, in FIG. 3, four events 42—42 having groups of pulses 41—41 have the same number of pulses 63, as shown in FIG. 5, but the strength count 62 will differ depending on the pattern of the envelopes 43—43 of the events shown in FIG. 4. By forming a ratio of the count 62 to the count 63 for each event 42, it has been found that there is a range of ratio values which indicate that the event was due to an SWE signal. In FIG. 3, the two events 42 in the left side of the waveform 40 are due to SWE, while the two events on the right side of the waveform were due to noise. The signal strength to pulse count ratios of the SWE events clearly differ from the ratio associated with the noise events.

Additionally, the counting of pulses 41—41 only takes place in response to the crossing of the envelope 43 above a threshold 51, this insures that all SWE events will be recorded. In the prior art, either particular segments of an operation were monitored (e.g., melting, cooling, expulsing, heating) or a continuous readout was required. Where particular aspects were monitored, SWE signals due to cracking occurring during other time periods could be missed, while continuous monitoring might be expensive and cumbersome, particularly where operations have to be monitored for minutes or even hours.

Although the instant technique has been found to be most effective during the continuous operation hereinbefore described, it is not so limited for the instant concepts are equally applicable to spot welding, or the like. Additionally, the exemplary embodiment is set forth in terms of digital implementation, but it should readily be apparent for one skilled in the art to execute the instant concepts using analog techniques.

What is claimed is:

1. A method of determining whether a detected signal is a stress wave emission, the method comprising the steps of:
   (a) determining a first value that is proportional to the number of pulses of the detected signal having an amplitude exceeding a preset threshold during a period of time;
   (b) determining a second value that is proportional to the area under an envelope of the detected signal during said time period;
   (c) forming a ratio of the area value to the pulse value; and
   (d) comparing the ratio so formed to a predetermined range of ratio values which are indicative of a stress wave emission.

2. The method as set forth in claim 1, wherein the period of time in which the steps (a) and (b) take place is determined by:
   forming an envelope of the detected signal prior to step (a); and
   permitting the determining steps (a) and (b) to proceed only when the detected signal envelope is above a predetermined threshold.

3. The method as set forth in claim 1 wherein step (a) is further characterized by:
   counting the number of pulses of the detected signal having an amplitude exceeding the preset threshold.

4. The method as set forth in claim 3 wherein step (b) is further characterized by:
   providing a continuous train of pulses in said time period in response to the amplitude of the envelope of the detected signal, the period of the pulses being inversely proportional to the amplitude of the signal envelope; and
   counting said pulses in the train of pulses in said time period.

5. An apparatus for determining whether a detected signal is a stress wave emission, the apparatus comprising:
   (a) means for determining a first value that is proportional to the number of pulses of the detected signal having an amplitude exceeding a preset threshold during a period of time;
   (b) means for determining a second value that is proportional to the area under an envelope of the detected signal during said time period;
   (c) means for forming a ratio of the area value to the pulse value; and
   (d) means for comparing the ratio so formed to a predetermined range of ratio values which are indicative of a stress wave emission.

6. The apparatus as set forth in claim 5 for determining the time period which comprises:
   means for forming an envelope of the detected signal:
   means for detecting when the amplitude of the envelope is above a predetermined threshold; and
   means responsive to the detecting means to enable the determining means (a) and (b) to determine the first and second values only when the signal envelope is above the predetermined threshold.

7. The apparatus as set forth in claim 6 which the second value determining means (b) is further characterized by:
   means for continuously converting the amplitude of the signal envelope during said time period into a continuous train of pulses having a period which is inversely proportional to the amplitude of the signal envelope; and
   means for counting said pulses in said train of pulses in said time period.

8. The apparatus as set forth in claim 5 wherein the first value determining means (a) is further characterized by:
   means for counting the number of pulses of the detected signal having an amplitude exceeding a preset threshold.

9. The apparatus as set forth in claim 5, which further comprises:
   means for indicating when the ratio falls within the range indicative of a stress wave emission signal.

* * * * *